United States Patent [19]

Fox, Jr.

[11] 4,195,094

[45] Mar. 25, 1980

[54] ZINC CONTAINING HYPOGLYCEMIC AGENTS

[75] Inventor: Charles L. Fox, Jr., Sherman, Conn.

[73] Assignee: Research Corporation, New York, N.Y.

[21] Appl. No.: 863,864

[22] Filed: Dec. 23, 1977

[51] Int. Cl.[2] ...................... C01B 25/08; C01B 35/02; C07F 3/06

[52] U.S. Cl. ................................ 424/289; 260/429.9; 424/245

[58] Field of Search ..................... 260/429.9; 424/245, 424/289

[56] References Cited

U.S. PATENT DOCUMENTS

| | | | |
|---|---|---|---|
| 2,507,537 | 5/1950 | Mellan | 260/239.6 |
| 2,968,158 | 1/1961 | Ruschig et al. | 424/321 |
| 3,157,700 | 11/1964 | Schmidt et al. | 260/553 D |
| 3,332,942 | 7/1967 | Breivogel et al. | 260/239.95 |
| 3,860,724 | 1/1975 | Bretschneider et al. | 424/321 |
| 3,899,521 | 8/1975 | Evers | 260/429.9 |
| 3,928,590 | 12/1975 | Wolf et al. | 424/245 |

OTHER PUBLICATIONS

Chemical Abstracts 67 (6) 26372f (1967).
Chemical Abstracts 55 (1) 777e (1961).
Chemical Abstracts 67 (3) 10032j (1967).
The Merck Index, Merck & Co., Inc., N. J., 9th Ed., pp. 572, 573, 580, 1223 (1976).

*Primary Examiner*—Helen M. S. Sneed
*Attorney, Agent, or Firm*—Cooper, Dunham, Clark, Griffin & Moran

[57] ABSTRACT

Zinc and cerium salts of known oral hypoglycemic agents, particularly sulfonylureas, are effective in lowering elevated blood sugar levels, such as are associated with diabetes.

10 Claims, No Drawings

ZINC CONTAINING HYPOGLYCEMIC AGENTS

BACKGROUND OF THE INVENTION

Various oral hypoglycemic agents such as those described in U.S. Pat. Nos. 2,968,158 and 3,860,724 and British Pat. No. 887,886 are known to be effective in reducing blood sugar levels in warm-blooded animals and also to be useful in the treatment of diabetes. Moreover, so-called trace metals are known to be generally important in human and animal metabolism. For example, zinc is known to be associated with insulin and pancreatic beta cells contain unusually large amounts of zinc. Changes in zinc content and granulation of beta cells parallel one another and substances which compete with insulin for zinc may induce release of insulin. Finally, a complex of aspartic acid, a compound not known to be a hypoglycemic agent or to possess hypoglycemic activity, with trivalent rare earths and zinc has been unexpectedly found to depress the level of sugar in blood and urine as disclosed in U.S. Pat. No. 3,899,521.

SUMMARY OF THE INVENTION

The present invention relates to metallic salts or compounds useful as oral hypoglycemic agents. The metallic portion thereof may be zinc and/or cerium and the non-metallic portion or moiety a known hypoglycemic agent, such as a sulfonylurea. Such compounds are particularly effective in reducing blood sugar levels in warm-blooded animals and in treating diabetes. The metallic salts or compounds of this invention are readily precipitated upon addition of a water-soluble, usually inorganic, zinc or cerium salt, such as zinc or cerium acetate, to a previously prepared alkali metal salt of the hypoglycemic agent, e.g. sulfonylurea. The alkali metal salts of the hypoglycemic agent, such as those of sodium and potassium, are particularly useful and are usually prepared by addition of an appropriate base, such as sodium hydroxide or potassium hydroxide, to the hypoglycemic agent.

Compositions in accordance with this invention are prepared which comprise an effective amount of the oral hypoglycemic agents described herein and a suitable carrier, e.g., corn starch or magnesium stearate.

Accordingly, it is an object of this invention to provide improved oral hypoglycemic agents and compositions including such hypoglycemic agents for use in lowering blood sugar levels in warm-blooded animals and in treating diabetes.

It is another object of this invention to provide methods of preparing these hypoglycemic agents and compositions and of using such agents and compositions to reduce elevated sugar levels in warm-blooded animals and to treat diabetes.

How these and other objects of this invention are achieved will become apparent in light of the accompanying disclosure and claims. In at least one embodiment of the practices of this invention at least one of the foregoing objects will be achieved.

DETAILED DESCRIPTION OF THE INVENTION

Novel compounds of this invention useful as oral hypoglycemic agents which have the structure MX, wherein M is a metal, such as zinc and/or cerium, and X is hypoglycemic agent, or hypoglycemic active moiety thereof, such as a sulfonylurea, have been prepared.

Specific hypoglycemic agents, the metallic salts of which have been prepared include tolbutamide, tolazamide, glibornuride, glibenclamid (Glyburide) and glybuthiazole. In accordance with this invention there is usually present one atom of zinc or cerium combined with two or three moles or moieties respectively of the hypoglycemic agent except for glyburide which combines with zinc in a ratio of one to one. Other ratios may possibly be formed, particularly with other known hypoglycemic agents, such as ratios of metal to hypoglycemic agent of two to one, two to three, three to two, etc.

Generally, the compounds of this invention are prepared by reacting one mole of zinc or cerium acetate with two or three moles respectively of an alkali metal salt of the hypoglycemic agents. For example, the alkali metal salts of sulfonylurea compounds are first prepared by dissolving or suspending in water the sulfonylurea and forming an alkali metal salt by addition of an inorganic metal base, such as sodium hydroxide or potassium hydroxide. In the case of tolbutamide, the sodium salt is readily available. The alkali metal salt is then reacted with an inorganic or organic zinc or cerium salt, such as zinc acetate or cerium acetate, and a precipitate results. The precipitate is washed, first with water, then with alcohol, and dried. The zinc and/or cerium-containing hypoglycemic compounds were characterized by examining their ultraviolet spectra. In each case the ultraviolet spectra closely resembles the ultraviolet spectra of the parent compounds, i.e., hypoglycemic moiety. For example, for sulfonylurea compounds there was a maximum at 209 mμ and another band at 225 mμ. The formation of the zinc salt was confirmed by atomic absorption spectroscopy.

Compositions useful as oral hypoglycemic agents in accordance with this invention comprise an effective amount of the metallic, zinc and/or cerium, hypoglycemic compounds described herein and a carrier. Carriers usefully employed include organic and/or inorganic materials, such as lactose, starch, talc, magnesium stearate, corn starch and the like. They can also contain other ingredients, including other non-zinc or non-cerium-containing hypoglycemic agents.

Metallic compounds prepared in accordance with this invention were tested for hypoglycemic activity by comparing their effect with that of their non-metallic or non-zinc or non-cerium-containing counterpart hypoglycemic agents, such as sulfonylureas, in normal rats. In these tests the rats were starved for four hours and then subcutaneously injected with 0.8–1.0 gram of dextrose per kilogram of body weight and their blood sugar levels then determined. The rats were then given orally varying doses of zinc or cerium containing sulfonylurea compounds of this invention in the range 10–100 mg per kg of body weight. The fast was continued during the experiment and blood samples were obtained two hours later and analyzed for dextrose. Normal rats which had not been injected with dextrose were similarly tested. The results obtained were as with many hypoglycemic agents, variable, but generally the blood sugar was lowered with the zinc and cerium containing compounds either in the same amount or to a slightly greater degree than with the parent sulfonylurea compounds. Cerium hypoglycemic compound salts gave better results than the corresponding zinc hypoglycemic compounds.

Experiments were also conducted with rats made "diabetic" by graded injections of Streptozotocin. The lowering of blood sugar levels was compared with that in normal rats that received either no additional sugar or the subcutaneous dextrose injection. Although there was considerable variation in the fasting blood sugar level of the normal animals prior to any testing, and such variations in the starting values made difficult an accurate evaluation of hypoglycemic activity, the same difficulty applied also to the sulfonylurea compounds per se. Nevertheless, the test data indicated that zinc-containing hypoglycemic compounds of this invention achieved lowering of the blood sugar levels in diabetic rats equivalent to or greater than that obtained with the parent zinc-free hypoglycemic compound and the cerium-containing hypoglycemic compounds were found to be more effective than zinc compounds.

It is recognized that lowering the blood sugar is not the only need of a diabetic organism. The zinc and/or cerium compounds of this invention have this effect and they also conceivably provide needed metals internally e.g. zinc to the pancreas at the point where zinc is necessary for the production or release of insulin to control blood sugar levels. Thus, a method is provided in accordance with this invention for lowering blood sugar levels in warm-blooded animals by administering orally to such animals an effective amount of the zinc-containing and/or cerium-containing hypoglycemic agents or compositions disclosed herein. Similarly, a method of treating diabetes is suggested which comprises orally administering to diabetics an effective amount of these compounds or compositions.

The following examples are intended to more clearly demonstrate the use of the compounds described in accordance with this invention. Examples 1 and 2 concern the reduction of blood sugar levels in warm-blooded animals. Example 3 concerns the use of the compounds described in providing zinc to the pancreas.

EXAMPLE 1

Different doses, e.g. 2.5 and 10 mg per kg body wt. of each of glyburide, zinc glyburide and cerium glyburide were administered to normal laboratory rats, at least four rats being tested in any given sample. The rats had previously been injected subcutaneously with 0.8 to 1.0 gram per kg of dextrose immediately prior to oral administration of the compounds and blood samples measured for sugar level. After two hours, blood samples were extracted and tested. Zinc glyburide was found to be significantly more effective in reducing blood sugar levels than the compound, glyburide, alone and cerium glyburide was essentially equivalent to zinc glyburide.

EXAMPLE 2

Tolbutamide, zinc tolbutamide and cerium tolbutamide were administered to normal rats in dosages ranging from 50 to 100 mg per kilogram, the rats having previously been subcutaneously injected with 0.8 to 1 gram of dextrose per kilogram of body weight and their blood sugar levels determined. Two hours after administration of the test compounds, blood sugar levels were again determined. In these tests zinc tolbutamide was found to be significantly more effective than tolbutamide in lowering blood sugar and cerium tolbutamide was found to be somewhat more effective than zinc tolbutamide.

EXAMPLE 3

The pancreas was removed from 24 freshly killed infant rats (9–10 days old). The 24 pancreases were divided into three groups of 8 each and each group weighed. Group 1 (8 pancreases) weighed 183.9 mg, Group 2 (8 pancreases) weighed 186.3 mg and Group 3 (8 pancreases) weighed 168.0 mg.

Three separate solutions were made up of zinc compounds. Solution 1 contained zinc glyburide and tissue culture medium. Solution 2 contained zinc acetate and tissue culture medium and Solution 3 contained zinc chloride and tissue culture medium. The zinc making up the zinc glyburide, zinc acetate and zinc chloride in these solutions contained the zinc isotope $Zn^{65}$. The zinc-containing solutions were counted on a gamma ray counter and the counts per minute were calculated for micrograms of zinc. For Solution 1 containing zinc glyburide, 4 mls of solution provided 21.9 μgm Zn. For Solution 2 containing zinc acetate, 4 mls of solution provided 21.2 μgm Zn and for Solution 3 containing zinc chloride, 4 mls of solution provided 22.6 μgm Zn.

The three groups of the twenty-four pancreases, Group 1, Group 2, and Group 3 were placed into the three solutions, Solution 1, Solution 2 and Solution 3, respectively and incubated at 37° C.

After one hour four pancreases were removed from each group and counted. After an additional hour a second group of four pancreases were removed and counted. The results were as follows:

| | Duration of Incubation | |
|---|---|---|
| | 1 Hour | 2 Hours |
| Group 1 - Solution 1 | | |
| Zinc glyburide | 1.3 μgm $Zn^{65}$ | 2.5 μgm $Zn^{65}$ |
| Group 2 - Solution 2 | | |
| Zinc acetate | 1.1 μgm $Zn^{65}$ | 1.4 μgm $Zn^{65}$ |
| Group 3 - Solution 3 | | |
| Zinc chloride | 1.2 μgm $Zn^{65}$ | 1.2 μgm $Zn^{65}$ |

After the pancreases were removed, they were weighed. The remaining solutions were then counted. The counts obtained indicated that per 100 mg of pancreas, the uptake of zinc was 3.5 μgm from the zinc glyburide solution, 2.6 μgm from the zinc acetate solution and 2.2 μgm from the zinc chloride solution.

The above results and data indicate that pancreatic tissues absorb zinc from zinc glyburide more readily than from zinc acetate or zinc chloride. The important point indicated by these tests is that zinc is transported to the pancreas in a greater amount by zinc glyburide than with zinc compounds, such as zinc acetate and zinc chloride, with compounds themselves do not exert or show a blood sugar lowering capability.

As should be obvious to one skilled in the art, many variations and modifications are possible in the practice of this invention without departing from the spirit and scope thereof as set forth in the claims which follow.

I claim:

1. A compound useful as an oral hypoglycemic agent which comprises a zinc salt of a sulfonyl urea compound selected from the group consisting of glyburide, glibornuride and tolbutamide.

2. A compound in accordance with claim 1 wherein the ratio of zinc to sulfonyl urea is in the range 2:1 to 1:3.

3. A compound in accordance with claim 1 wherein said sulfonyl urea is glyburide.

4. A compound in accordance with claim 3 wherein said ratio of zinc to sulfonyl urea is 1:1.

5. A composition useful as an oral hypoglycemic agent which comprises an effective amount of a zinc salt of a sulfonyl urea and a suitable physiologically acceptable carrier.

6. A composition in accordance with claim 5 wherein said sulfonyl urea is selected from the group consisting of glyburide, glibornuride, and tolbutamide.

7. A method of lowering blood sugar levels in warm-blooded animals which comprises administering orally to said animals an effective amount of a compound in accordance with claim 1.

8. A method of lowering blood sugar levels in warm-blooded animals which comprises administering orally to said animals an effective amount of a composition in accordance with claim 5.

9. A method of treating diabetes which comprises administering to diabetic subjects an effective amount of a compound in accordance with claim 1.

10. A method of treating diabetes which comprises administering to diabetic subjects an effective amount of a composition in accordance with claim 5.

* * * * *